(12) United States Patent
Ng et al.

(10) Patent No.: US 12,299,886 B2
(45) Date of Patent: *May 13, 2025

(54) SYSTEMS AND METHODS FOR DETECTING POTENTIAL MALIGNANCIES

(71) Applicant: Iterative Scopes, Inc., Cambridge, MA (US)

(72) Inventors: Jonathan Ng, Cambridge, MA (US); Sloane Allebes Phillips, Cambridge, MA (US); Amit Ranade, Cambridge, MA (US); Daniel Wang, Cambridge, MA (US); Perikumar Mukundbhai Javia, Cambridge, MA (US); Avi Walden, Cambridge, MA (US); Austin Wang, Cambridge, MA (US); Evan Wlodkowski, Cambridge, MA (US); Samriddhi Dhakal, Cambridge, MA (US)

(73) Assignee: Iterative Scopes, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/603,460

(22) Filed: Mar. 13, 2024

(65) Prior Publication Data

US 2024/0296561 A1     Sep. 5, 2024

Related U.S. Application Data

(63) Continuation of application No. 16/934,777, filed on Jul. 21, 2020, now Pat. No. 11,961,225.

(51) Int. Cl.
*G06T 7/00*     (2017.01)
*A61B 1/00*     (2006.01)
*A61B 1/31*     (2006.01)

(52) U.S. Cl.
CPC ........ *G06T 7/0012* (2013.01); *A61B 1/00004* (2013.01); *A61B 1/00016* (2013.01);
(Continued)

(58) Field of Classification Search
CPC ......... G06T 7/0012; G06T 2207/10016; G06T 2207/20084; G06T 2207/10068;
(Continued)

(56) References Cited

U.S. PATENT DOCUMENTS 10,510,144 B2    12/2019   Zur
10,639,104 B1    5/2020    Barral et al.
(Continued)

OTHER PUBLICATIONS

Klare et al., "Automated polyp detection in the colorectum: a prospective study (with videos)," Gastrointestinal Endoscopy, Mar. 2019, 89(3):576-582.

(Continued)

*Primary Examiner* — Amandeep Saini
*Assistant Examiner* — Denise G Alfonso
(74) *Attorney, Agent, or Firm* — Fish & Richardson P.C.

(57) ABSTRACT

One or more machine learning techniques can be used to identify locations of potential malignancies within images (e.g., video images) captured during a medical procedure, such as an endoscopic procedure. The images can be displayed, in real-time, on a display unit. The images can be displayed with a graphical overlay that isolates the identified locations of potential malignancies.

20 Claims, 6 Drawing Sheets

(52) U.S. Cl.
CPC ............... *A61B 1/0005* (2013.01); *A61B 1/31* (2013.01); *G06T 2207/10016* (2013.01); *G06T 2207/10068* (2013.01); *G06T 2207/20084* (2013.01); *G06T 2207/30096* (2013.01); *G06T 2210/12* (2013.01)

(58) Field of Classification Search
CPC ....... G06T 2207/30096; G06T 2210/12; G06T 2200/24; G06T 2207/20081; G06T 2207/30168; A61B 1/00004; A61B 1/00016; A61B 1/0005; A61B 1/31; A61B 1/00009

See application file for complete search history.

(56) References Cited

U.S. PATENT DOCUMENTS

| | | | |
|---|---|---|---|
| 10,810,460 | B2 | 10/2020 | Dinh et al. |
| 11,100,633 | B2 | 8/2021 | Dinh et al. |
| 11,195,052 | B2 | 12/2021 | Dinh et al. |
| 11,961,225 | B2 | 4/2024 | Ng et al. |
| 2018/0253839 | A1 | 9/2018 | Zur |
| 2018/0353244 | A1* | 12/2018 | Kashima ............... A61B 18/00 |
| 2019/0026608 | A1 | 1/2019 | Hsieh et al. |
| 2019/0200977 | A1 | 7/2019 | Shelton et al. |
| 2019/0297276 | A1* | 9/2019 | Sachdev ............... G16H 30/40 |
| 2020/0380675 | A1 | 12/2020 | Golden et al. |
| 2021/0012868 | A1 | 1/2021 | Wolf et al. |
| 2021/0274999 | A1* | 9/2021 | Kubota ............. A61B 1/00045 |
| 2022/0028059 | A1 | 1/2022 | Ng et al. |

OTHER PUBLICATIONS

Stidham et al., "Performance of a Deep Learning Model vs Human Reviewers in Grading Endoscopic Disease Severity of Patients With Ulcerative Colitis," JAMA Network Open, May 2019, 2(5):e193963, 10 pages.

Takenaka et al., "Development and Validation of a Deep Neural Network for Accurate Evaluation of Endoscopic Images From Patients with Ulcerative Colitis," Gastroenterology, Jun. 2020, 158(8):2150-2157.

* cited by examiner

SYSTEMS AND METHODS FOR DETECTING POTENTIAL MALIGNANCIES

CROSS-REFERENCE TO RELATED APPLICATIONS

This application is a continuation application of and claims the benefit of priority under 35 U.S.C. § 120 to U.S. application Ser. No. 16/934,777, filed on Jul. 21, 2020, the entire contents of which are hereby incorporated by reference.

TECHNICAL FIELD

This disclosure generally relates to systems and methods for detecting potential malignancies, such as polyps, during medical procedures.

BACKGROUND

Endoscopy refers to a nonsurgical procedure used to examine a person's digestive tract. Typically, an endoscope, which is a flexible tube that includes a light and camera, is placed within a patient's digestive tract so that a doctor can view images (e.g., still images and/or video) of the patient's digestive tract. For example, during an upper endoscopy, an endoscope is passed through the mouth and throat into the esophagus of a patient, allowing a doctor to view the esophagus, stomach, and upper part of the small intestine. Similarly, an endoscope can be passed into the large intestine of a patient through the rectum to examine this area of the intestine (e.g., a colonoscopy). Endoscopic procedures allow physicians to evaluate several medical conditions, such as causes of stomach pain, appearances of ulcers, bleeding in the digestive tract, and detection of potential malignancies (e.g., polyps).

SUMMARY

In an aspect, a data processing system for improving malignancy detection in individuals is provided. The system includes a computer-readable memory comprising computer-executable instructions. The system includes at least one processor executing executable logic including at least one artificial neural network trained to identify visual representations of malignancies in an image, wherein when the at least one processor is executing the computer-executable instructions, the at least one processor is configured to carry out one or more operations. The one or more operations include receiving, in real-time, spatially arranged image data associated with a plurality of images from an imaging device. The one or more operations includes generating a plurality of processed images by processing the spatially arranged image data through one or more data structures storing one or more portions of executable logic included in the artificial neural network to identify one or more pixels of the spatially arranged image data representing a location of a potential malignancy in an individual as the spatially arranged image data is received from the imaging device. The one or more operations include causing, in real-time, a display unit to render the plurality of processed images, in which one or more processed images of the displayed plurality of processed images includes one or more graphical overlays generated by the at least one processor unless one or more of: a surgical tool is detected in the one or more processed images; or a image quality metric of the one or more processed images does not exceed a quality metric threshold; each of the one or more graphical overlays isolates one or more image locations; and each of the one or more image locations represents at least one pixel representing a location of a potential malignancy in the individual.

The amount of time between receiving the spatially arranged image data and causing the display unit to display the plurality of processed images can be less than 60 milliseconds. The spatially arranged image data can be received through a video capture card that is communicatively coupled to an endoscopic processing unit that comprises the imaging device. The displayed plurality of processed images can include at least one visual indicator that indicates the displayed plurality of processed images correspond to spatially arranged image data that has been processed by the at least one processor.

The operations can further include causing the display unit to display an indicator that indicates a potential malignancy has been identified in a previously displayed processed image that did not include a graphical overlay isolating one or more image locations corresponding to that potential malignancy. The graphical overlay can include a bounding box. The potential malignancy can include a polyp. The imaging device can include an endoscopic imaging device. The at least one processor can be further configured to be communicatively coupled to a cloud-computing environment and to transmit the spatially arranged image data to the cloud-computing environment.

In an aspect, a system is provided. The system includes a video capture card configured to receive, from an endoscopic processing unit, spatially arranged image data captured by an endoscopic imaging device of the endoscopic processing unit. The system includes a data processing system including one or more elements of the previously described data processing system. The system includes a display switch configured to be communicatively coupled to the display unit, the data processing system, and the endoscopic processing unit, the display switch being further configured to allow displaying of either the plurality of processed images or a plurality of original images corresponding to the spatially arranged image data.

These and other aspects, features, and implementations can be expressed as methods, apparatus, systems, components, program products, methods of doing business, means or steps for performing a function, and in other ways, and will become apparent from the following descriptions, including the claims.

Implementations can include one or more of the following advantages. Image data can be captured during an endoscopic procedure using an imaging device such as an endoscope. The image data can be transmitted to one or more machine learning systems trained to identify locations of potential malignancies, such as polyps, based on the captured image data. In some implementations, when given a set of images, the machine learning system is capable of correctly detecting at least 87% of all polyps shown (e.g., at least one image of at least 87% of the polyps presented in the set of images will be corrected detected and identified by the machine learning system). Similarly, in some implementations, when given a set of images the machine learning system is capable of making a determination that the image does not contain a polyp, that determination is correct at least 98.7% of the time (e.g., the machine learning system is likely to be correct 98.7% of the times the machine learning system makes a "does not contain polyp" prediction). The images captured during the endoscopic procedure can be displayed on a display unit, such as a color monitor. In some implementations, when the machine learning system identifies a location of a potential malignancy, the location of the potential malignancy is highlighted on the display unit in real-time. Furthermore, as opposed to conventional technology, the machine learning system can detect the presence of a surgical tool and remove the highlight on the display unit to prevent the highlight from obscuring the surgical tool (for example, during an operation). Thus, the systems and methods described herein can provide means for enhanced potential malignancy detection during an endoscopic procedure by identifying potential malignancies that may not be visible to the average human eye and providing means for visually highlighting the locations of these potential malignancies in real-time during the endoscopic procedure while not hindering the surgical processes of the endoscopic procedure. When compared with conventional systems, the systems and methods described in this specification can lead to several health benefits, including earlier detection, more accurate detection, and facilitate a lower risk of cancer.

These and other aspects, features, and implementations can be expressed as methods, apparatus, systems, components, program products, means or steps for performing a function, and in other ways.

These and other aspects, features, and implementations will become apparent from the following descriptions, including the claims.

DETAILED DESCRIPTION

Figure 1:
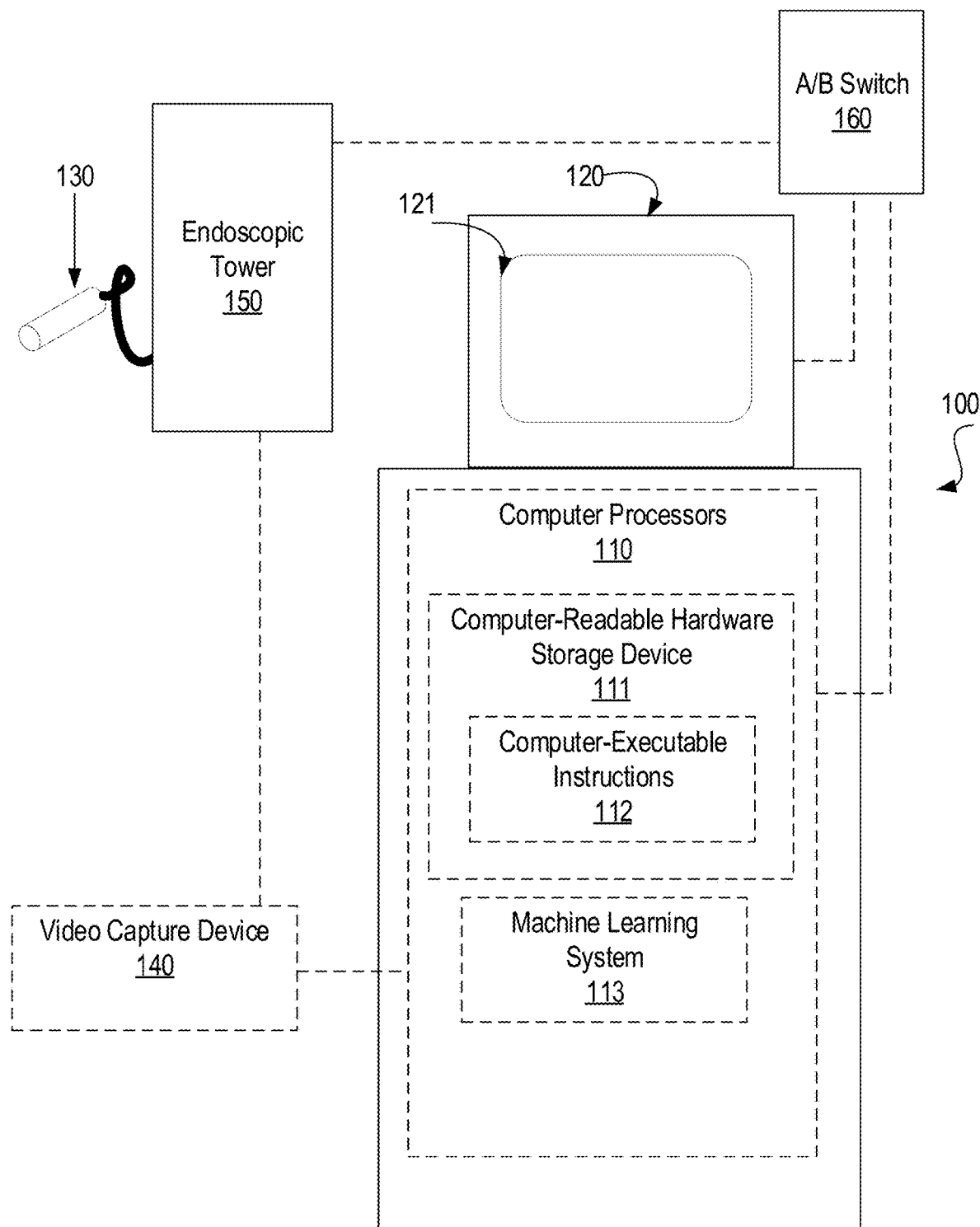
FIG. 1 shows a data processing system for improving the accuracy and resolution of potential malignancy detection in individuals, according to one or more implementations of the present disclosure.

An adenoma detection rate (ADR) is a reportable rate of a physician's ability to find adenomatous polyps, which can be measured as the number of procedures where physician identifies and resects an adenomatous polyp divided by the total procedures completed by the physician. An adenomatous polyp is defined as a proliferation of glandular tissue of the colon that may be benign but may be a precursor lesions to colorectal cancer. In some cases, villous histology, increasing polyp size, and high-grade dysplasia may be risk factors for focal cancer within an individual adenoma. The ADR has been the "gold standard" in measuring a provider's colonoscopy quality. Currently, ADRs greater than 20% are considered acceptable, with 30% of physicians having an ADR below this rate. Some studies have shown that for each 1% increase in ADR, there was an associated 3% reduction in the risk of a patient getting cancer. Due to the potential reduction in cancer risks, it may be desirable to implement technology that can aid in the detection of potential malignancies, such as polyps, during an endoscopic procedure.

Furthermore, while some conventional technologies that exploit machine learning can be used to identify potential malignancies in images, these conventional technologies typically do so using historic images from medical procedures that have already occurred. However, because some sighted polyps are usually removed during the medical procedure, it may be desirable to provide potential malignancy detection in real-time, as the medical procedure is being conducted.

The present disclosure provides systems and methods for detecting potential malignancies, such as polyps, during medical procedures. Image data corresponding to a plurality of images are captured using an imaging device (e.g., endoscope) during a medical procedure, such as a colonoscopy. The image data is transmitted to a machine learning system trained to identify locations of potential malignancies. The machine learning system identifies, based on the image data, potential locations of malignancies in the images. In real-time, the images are displayed on a display unit. As they are displayed on the display unit, the images can include an overlay that highlights the potential malignancy locations. Therefore, as a physician conducts the medical procedure, locations of potential malignancies, including those that may be difficult to see (e.g., relative to a person with average human eyesight), will be brought to the physician's attention in real-time. Consequently, the systems and methods can increase the rate at which potential malignancies are detected and removed.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all embodiments or that the features represented by such element may not be included in or combined with other elements in some embodiments.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (e.g., a bus), as may be needed, to affect the communication.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Several features are described hereafter that can each be used independently of one another or with any combination of other features. However, any individual feature may not provide any of the advantages discussed above or might only provide one of the advantages discussed above. Although headings are provided, data related to a particular heading, but not found in the section having that heading, may also be found elsewhere in this description.

FIG. 1 shows an environment 101 including a data processing system 100 for improving the accuracy and resolution of potential malignancy detection in individuals (relative to prior method for malignancy detection), according to one or more embodiments of the present disclosure. The system 100 includes computer processors 110, a display unit 120, a video capture device 140, and an A/B switch 160 (sometimes referred to as a display switch in this specification).

The system 100 is configured to be operated in conjunction with an endoscopic tower 150 (sometimes referred to as an endoscopic processing unit in this specification). The endoscopic tower includes an imaging device 130 that is configured to capture image data and also includes image processing means for processing the captured image data. In some implementations, the imaging device 130 is an endoscope. An endoscope is an illuminated optical, thin, and tubular instrument (e.g., borescope) used to examine internal organs like the throat or esophagus. The endoscope can be shaped and configured to target specific organs, such as the bladder, kidney, bronchus, colon, and/or pelvis. In some implementations, the endoscope is flexible and includes a camera on one end. The camera can capture image data in the form of still images and/or video. The image data can take the form of several image data formats, such as RAW, JPEG, PNG, etc. In some implementations, the imaging device 130 includes a digital camera that uses a charged-coupled device (CCD) and/or complementary metal oxide semiconductor (CMOS) to convert photons to electrons for digital processing.

The video capture device 140 is configured to be communicatively coupled to the computer processors 110 and the endoscopic tower 150 and configured to store the images captured by the imaging sensor 130. For example, the video capture device 140 can be a video card that can receive image data from the imaging device 130 (via the endoscopic tower 150) representing one or more captured images, consolidate the captured images into video data, store the video data in memory, and transmit the video data to the computer processors 110 for further processing (as discussed later). The video capture device 140 can be integrated with the computer processors 110 or can be separate from the computer processors 110. Particular uses of the video data stored and transmitted by the video capture device 140 are described later with reference to FIG. 4.

The A/B switch 160 is communicatively coupled to the endoscopic tower 150, the computer processors 110, and the display unit 120. The A/B switch 160 is configured to receive processed image data (for example, video data) from the endoscopic tower 150 and cause the display unit 120 to display images (such as, video) of the processed image data received from the endoscopic tower 150. As will be discussed later in more detail, the A/B switch 160 is also configured to receive processed image data (for example, video data) from the computer processors 110, and cause the display device 120 to display images (such as video) of the processed image data received from the computer processors 110. A user can use the A/B switch 160 to toggle between causing the display unit 160 to display images from the processed image data of the endoscopic tower 150 and images from the processed image data of the computer processors 110.

The computer-readable hardware storage device 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable hardware storage device 111 includes code-segment (or other executable logic) having executable instructions.

The computer processors 110 are communicatively coupled to the video capture device 140 and configured to receive spatially arranged image data (e.g., video data) corresponding with one or more images captured by the imaging device 130. In some implementations, the computer processors 110 include a general purpose processor. In some implementations, the computer processors 110 include a graphic processing unit (GPU). In some implementations, the computer processors 110 include at least one applicable inference processor, accelerated processor which can be utilized in half, single, or double precision (16, 32, or 64 bit floating-point) calculation. The computer processors 110 can also include lots of compute unified device architecture (CUDA) cores, etc., or a combination of thereof. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112.

The display unit 120 is communicatively coupled to the computer processors 110 and the endoscopic tower 150 via the A/B switch 160. The display unit 120 is an electronic display device. The display unit 120 can be configured to act as a touchscreen display device. In some implementations, the display unit 120 includes a user interface 121. In some implementations, the user interface 121 is a graphical user interface (GUI). The user interface 121 is configured to allow a user of the system 100 to interact with the system 100 through graphical icons and visual indicators. The user interface 121 can use a windows, icons, menus, pointer paradigm (WIMP) to allow a user to interact with the system 100. In some implementations, the user interface 121 cooperates with the 120 to provide a user with a touchscreen GUI. Additionally, or alternatively, the user interface 121 can include one or more input devices such as a mouse and/or keyboard communicatively coupled with the system 100.

The user interface 121 can also use a post-WIMP paradigm typically found in touchscreen-based GUIs. In some implementations, the user interface 121 is configured to display images in the form of still photographs and/or videos.

In some implementations, the machine learning system 113 is integrated with the computer processors 110. In some implementations, the machine learning system 113 is separate from the computer processors 110. In some implementations, the machine learning system 113 includes a convolutional neural network (CNN).

A convolutional neural network (CNN) can be configured based on a presumption that inputs to the neural network correspond to image pixel data for an image or other data that includes features at multiple spatial locations. For example, sets of inputs can form a multi-dimensional data structure, such as a tensor, that represent color features of an example digital image (e.g., an image of the surroundings of a vehicle). In some implementations, inputs to the neural network correspond to a variety of other types of data, such as data obtained from different devices and sensors of a vehicle, point cloud data, audio data that includes certain features or raw audio at each of multiple time steps, or various types of one-dimensional or multiple dimensional data. A convolutional layer of the convolutional neural network can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which a system performs the computations can be based on specific properties for each layer of an example multi-layer neural network or deep neural network that supports deep neural net workloads. A deep neural network can include one or more convolutional towers (or layers) along with other computational layers. In particular, for example computer vision applications, these convolutional towers often account for a large proportion of the inference calculations that are performed. Convolutional layers of a CNN can have sets of artificial neurons that are arranged in three dimensions, a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R, G, B. A convolutional layer of a neural network of the machine learning system 113 computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer. That is, for each kernel or set of kernels, the machine learning system 113 can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The machine learning system 113 can then compute a dot product from the overlapped elements. For example, the machine learning system 113 can convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The machine learning system 113 can convolve each kernel over each input of an input volume. The machine learning system 113 performs this convolution operation by, for example, moving (or sliding) each kernel over each input in the region.

The machine learning system 113 moves each kernel over inputs of the region based on a stride value for a given convolutional layer. For example, when the stride is set to 1, then the machine learning system 113 moves the kernels over the region one pixel (or input) at a time. Likewise, when the stride is 2, then the machine learning system 113 moves the kernels over the region two pixels at a time. Thus, kernels may be shifted based on a stride value for a layer and the machine learning system 113 can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the machine learning system 113 produces a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the neural network.

An example convolutional layer can have one or more control parameters for the layer that represent properties of the layer. For example, the control parameters can include a number of kernels, K, the spatial extent of the kernels, F, the stride (or skip), S, and the amount of zero padding, P. Numerical values for these parameters, the inputs to the layer, and the parameter values of the kernel for the layer shape the computations that occur at the layer and the size of the output volume for the layer. In one implementation, the spatial size of the output volume is computed as a function of the input volume size, W, using the formula (W−F+2P)/S+1. For example, an input tensor can represent a pixel input volume of size [227×227×3]. A convolutional layer of a neural network can have a spatial extent value of F=11, a stride value of S=4, and no zero-padding (P=0). Using the above formula and a layer kernel quantity of K=96, the machine learning system 113 performs computations for the layer that results in a convolutional layer output volume of size [55×55×96], where 55 is obtained from [(227−11+0)/4+1=55].

The computations (e.g., dot product computations) for a convolutional layer, or other layers, of a neural network involve performing mathematical operations, e.g., multiplication and addition, using a computation unit of a hardware circuit of the machine learning system 113. The design of a hardware circuit can cause a system to be limited in its ability to fully utilize computing cells of the circuit when performing computations for layers of a neural network.

Based on the aforementioned techniques, the machine learning system 113 is configured to identify locations of potential malignancies in images. In some implementations, potential malignancies include polyps. In some implementations, given a set of images, the machine learning system 113 is capable of correctly detecting at least 87% of all polyps shown (e.g., at least one image of at least 87% of the polyps presented in the set of images will be correctly detected and identified). In some implementations, when given a set of images, and the machine learning system 113 is capable of making a determination that an image does not contain a polyp, and that determination is correct at least 98.7% of the time (e.g., it is likely to be correct 98.7% of the times the machine learning 113 system makes a "does not contain polyp" prediction).

In some implementations, the machine learning system 113 includes other types of digital neural networks, such as a recurrent neural network (RNN), a radial basis function network, a deconvolution network, a variational auto-encoder (VAE), generative adversarial network (GAN) and so forth. In some implementations, the machine learning system 113 is trained to detect surgical tools (e.g., scalpels)

When the computer processors 110 execute the computer-executable instructions 112, the computer processors 110 carry out one or more operations. In some implementations, when the computer processors 110 execute the computer-executable instructions 112, the computer processors 110 are configured to receive, in real-time, spatially arranged image data associated with a plurality of images from an imaging device, such as the imaging device 130 of the endoscopic tower 150 (for example, via the video capture device 140). During a medical procedure, the imaging device 130 can be inserted within a patient and capture several images. The imaging device 130 can transmit image data corresponding with the captured images to the computer processors 110 and/or the machine learning system 113 via the video capture device 140.

When the computer processors 110 execute the computer-executable instructions 112, the computer processors 110 are configured to generate a plurality of processed images by processing the spatially arranged image data through one or more data structures storing one or more portions of executable logic included in an artificial neural network (e.g., the machine learning system 113) to identify one or more pixels of the spatially arranged image data representing a location of a potential malignancy in an individual as the spatially arranged image data is received from the imaging device 113. In some implementations, as the image data is received, the machine learning system identifies locations of potential malignancies (e.g., polyps) using one or more of the aforementioned techniques.

Figure 6:
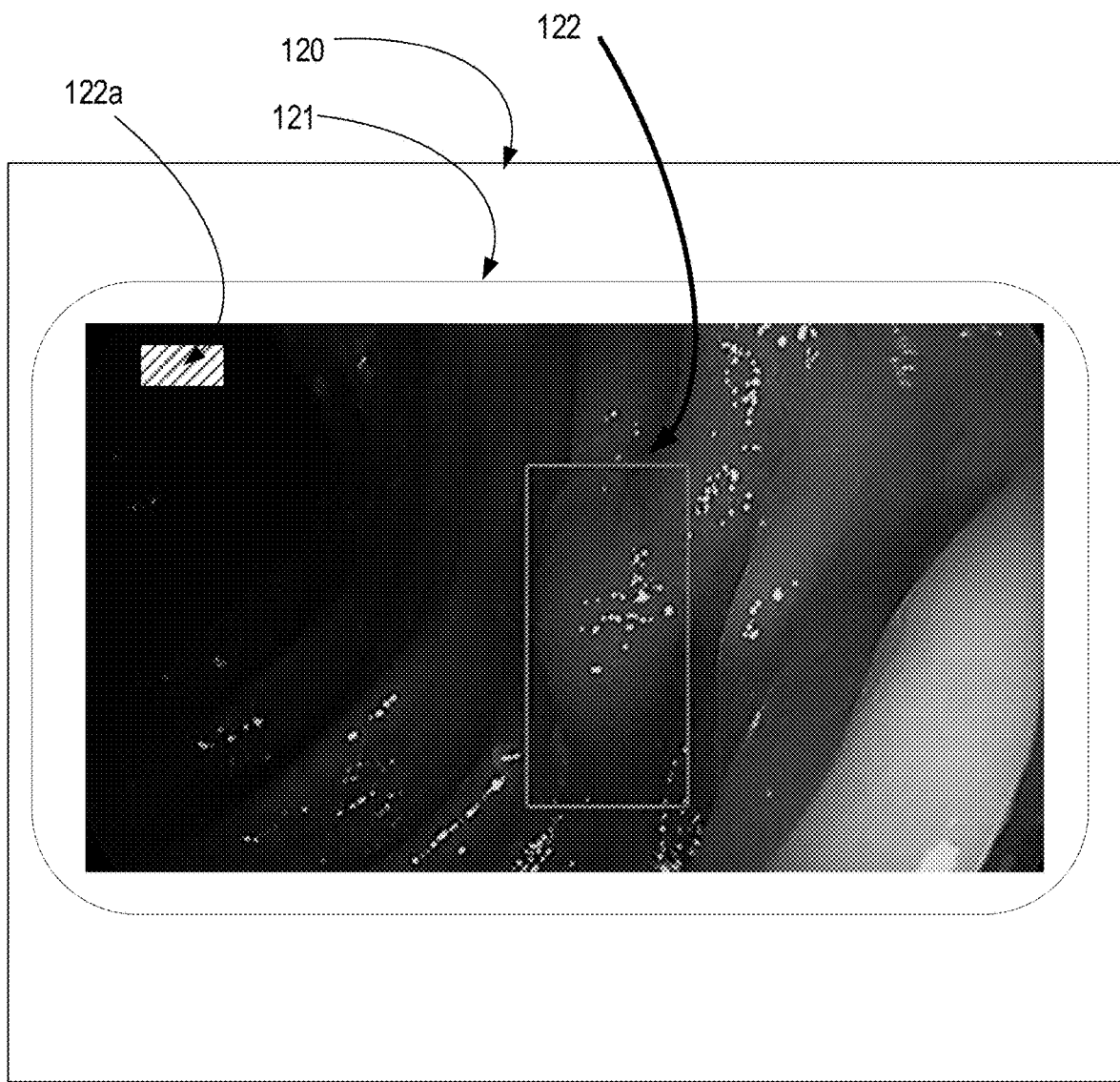
FIG. 6 shows an example of an image having a graphical overlay being displayed by a display unit.

When the computer processors 110 execute the computer-executable instructions 112, the computer processors 110 are configured to cause, in real-time, the display unit 120 to render the plurality of processed images corresponding to the image data by transmitting the processed image data to the A/B switch 160. In some implementations, one or more of the displayed processed images includes one or more graphical overlays generated by the computer processors 110. FIG. 6 shows an example of an image having a graphical overlay 122 being displayed by the display unit 120. As shown, the graphical overlay 122 isolates the one or more image locations having a detected potential malignancy. In the illustrated implementation, the graphical overlay 122 includes a bounding box. However, other implementations include other types of isolating means, such as color segmenting, color highlighting, and so forth. In some implementations, as shown in FIG. 6, one or more indicators 122a can be displayed along with the plurality of processed images. The one or more indicators 122a can indicate at least one of: that the images being displayed are the processed images from the computer processors 110 and that a polyp was detected in a previously displayed image but the duration of the time the overlay 122 was displayed did not satisfy a threshold amount of time (which can be advantageous if, for example, the operator of the endoscopic imaging device moved the device too quickly through the patient, e.g., the overlay was only displayed for 5 milliseconds, and therefore may not have been detected by the medical personnel).

Referring back to FIG. 1, as previously described, the spatially arranged data can be received in real-time, and the display unit 120 can be caused to display the images in real-time. In some implementations, the amount of time between receiving the spatially arranged image data and causing the display unit 120 to display the plurality of images is short enough to ensure that the viewed images/video is absent of substantial jitter. For example, the time between capture and display can be less than 60 milliseconds.

Although the data processing system 100 is shown as including computer processors 110, a machine learning system 113, a video capture device 140, an A/B switch 160, and a display unit 120, some implementations are not so limited. For example, in some implementations, the data processing system 100 includes the imaging device 130. The endoscopic tower 150 can include a display unit in addition to, or in alternative to, the data processing system 100. In such instances, the data processing system 100 can display the images captured by the imaging device 130 of the endoscopic tower or, in implementations in which the data processing system 100 does not include the display unit 120, the data processing system 100 can cause the aforementioned overlay to be displayed on the display unit 120 of the endoscopic tower 150.

Figure 2:
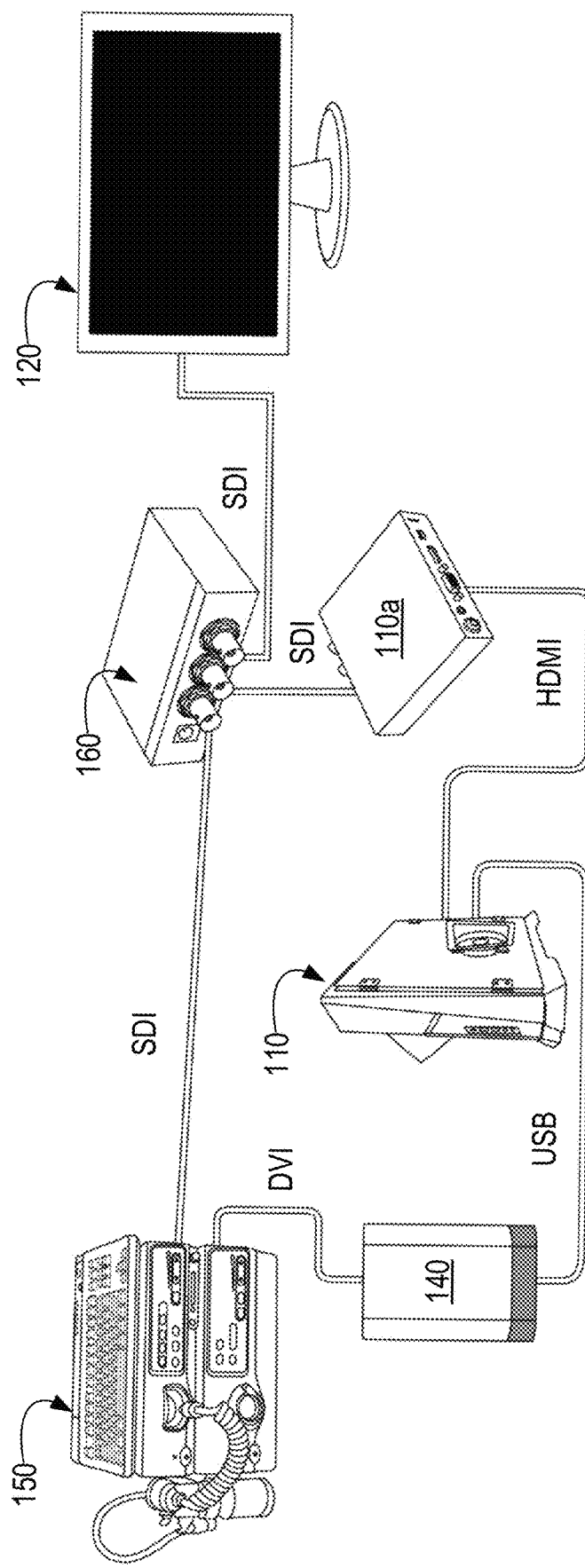
FIG. 2 shows an implementation of the data processing system of FIG. 1.

FIG. 2 shows an implementation of the system 100 illustrated in FIG. 1. As shown, the endoscopic unit is coupled to the video capture card 140 using a digital visual interface cable, the video capture card is coupled to the computer processors 110 using a universal serial bus (USB) cable, the computer processors 110 are coupled to the a/b switch 160 through a high definition multimedia interface (HDMI) to serial digital interface (SDI) converter, and the endoscopic unit is coupled to the a/b switch using an SDI cable. As indicated previously, in some implementations, the video capture card 140 is integrated with the computer processors 110. Although the shown implementations describes specific types of interfaces, converters, and means of connections (e.g., cables), other implementations may alternatively, or additionally, include other types of interfaces, converters, and means of connections.

Figure 3:
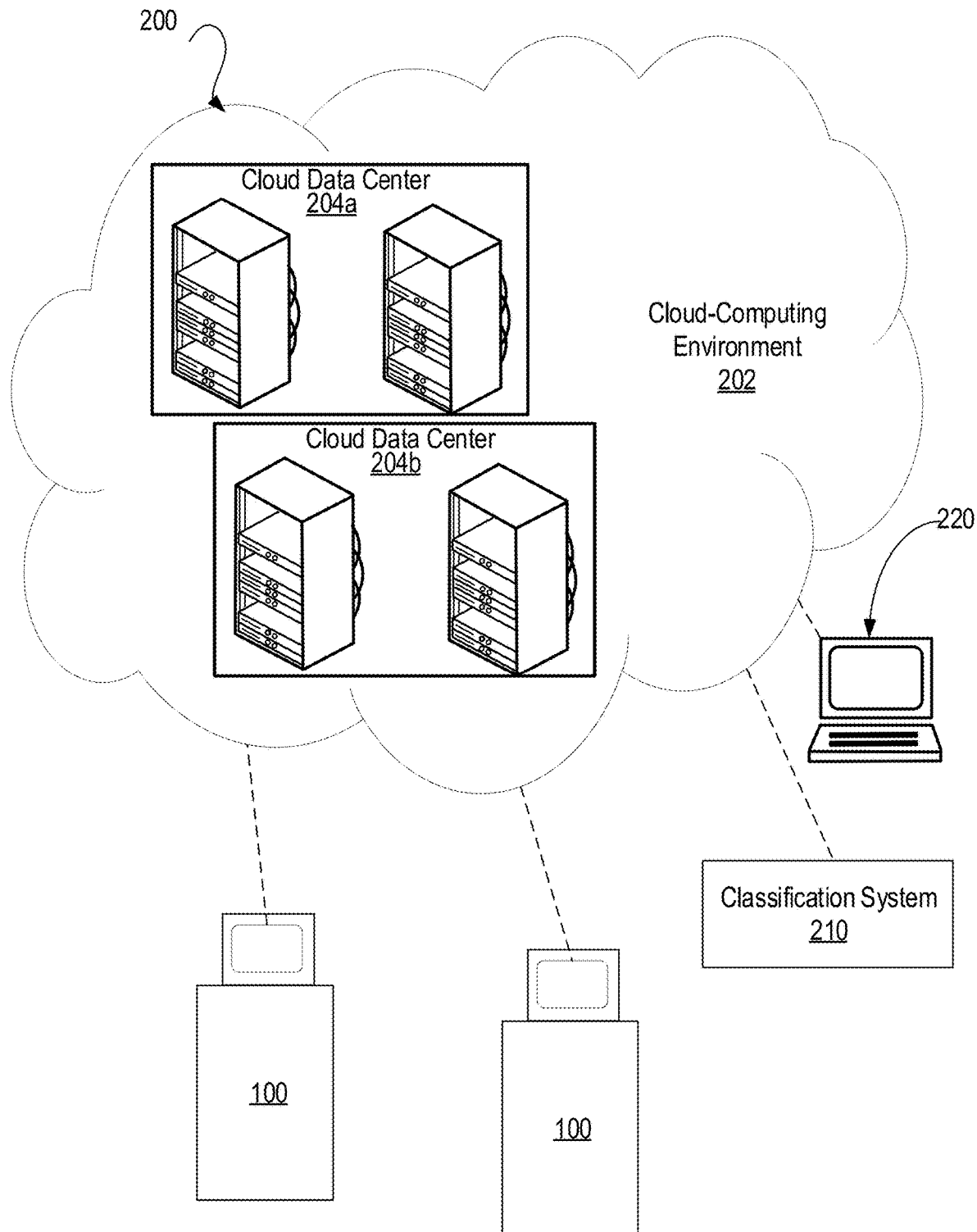
FIG. 3 shows a system for providing malignancy detection training and reporting, according to one or more embodiments of the present disclosure.

FIG. 3 shows a system 200 for providing malignancy detection training and reporting, according to one or more embodiments of the present disclosure. The system 200 includes one or more of the data processing systems 100 for improving potential malignancy detection in individuals previously discussed with reference to FIG. 1. The system 200 includes a classification system 210, a cloud-computing environment 202, cloud data centers 204a, 204b, a classification system 210, and computing systems 220. In this example, a cloud data center includes a hardware storage device that stores data records (including various fields), data structures (including various fields and storing executable logic) and other structured data.

The cloud-computing environment 202 is configured to perform one or more cloud computing techniques. Cloud computing can refer to a model of service delivery for enabling convenient, on-demand network access to a shared pool of configurable computing resources (e.g. networks, network bandwidth, servers, processing, memory, storage, applications, virtual machines, and services). The cloud-computing environment 200 can include one or more large cloud data centers that house the machines used to deliver the services provided by the cloud. In the shown implementation, the cloud-computing environment 202 includes cloud data centers 204a, 204b that are interconnected through the cloud-computing environment 202. The data centers 204a, 204b provide cloud computing services to computer systems 220 connected to the cloud-computing environment 202.

In general, a cloud data center, for example the cloud data centers 204a, 204b as shown, refers to the physical arrangement of servers that make up a cloud-computing environment. For example, servers are physically arranged in the cloud data centers 204a, 204b into rooms, groups, rows, and racks. In some implementations, the cloud data centers 204a, 204b have one or more zones, which include one or more rooms of servers. Each room has one or more rows of servers, and each row includes one or more racks. Each rack includes one or more individual server nodes. In some implementation, servers in zones, rooms, racks, and/or rows are arranged into groups based on physical infrastructure requirements of the datacenter facility, which include power, energy, thermal, heat, and/or other requirements. In some implementations, the data centers 204a, 204b have many computing systems distributed through many racks.

The cloud-computing environment 202 includes cloud data centers 204a, 204b, along with the network and networking resources (for example, networking equipment, nodes, routers, switches, and networking cables) that interconnect the cloud data centers 204a, 204b, and help facilitate the computing systems' 220 access to cloud computing services. In some implementations, the network represents any combination of one or more local networks, wide area networks, or internetworks coupled using wired or wireless links deployed using terrestrial or satellite connections. Data exchanged over the network, is transferred using any number of network layer protocols, such as Internet Protocol (IP), Multiprotocol Label Switching (MPLS), Asynchronous Transfer Mode (ATM), Frame Relay, etc. Furthermore, in implementations where the network represents a combination of multiple sub-networks, different network layer protocols are used at each of the underlying sub-networks. In some implementations, the network represents one or more interconnected internetworks, such as the public Internet.

The computing systems 220 or cloud computing services consumers are connected to the cloud-computing environment 202 through network links and network adapters. In an implementation, the computing systems 220 are implemented as various computing devices, for example servers, desktops, laptops, tablet, smartphones, Internet of Things (IoT) devices, and consumer electronics. In an implementation, the computing systems 202 are implemented in or as a part of other systems.

The systems 100 are communicatively coupled to the cloud-computing environment 202 and are capable of transmitting the image data captured by an imaging device (such as the image device 130 discussed previously with reference to FIG. 1) to the cloud-computing environment for storage (e.g., using the cloud data centers 204a, 204b). This image data can be retrieved by the computing systems 220 and/or the classification system 210. The computing systems 220 can retrieve the image data and display the corresponding images on a user interface of the computing systems 220. Thus, personnel such as medical leadership (e.g., Head of Endoscopy) can access and view the images captured by each system 100. In some implementations, the accessed images include the graphical overlays generated by the computer processors 110 that isolate the locations of potential malignancies.

The classification system 210 includes an interface (e.g., a computing device with a user interface) that allows a user to retrieve the images perform one or more operations with respect to the images. In some implementations, the images are the images processed by the systems 100. In some implementations, the cloud-computing environment stores images related to other medical procedures (e.g., endoscopy procedures) from other sources that are not integrated with the systems 100 and the classification system 210 can retrieve and display these images. In some implementations, the classification system 210 includes an application that allows a user to label potential malignancy locations within the received images. This labeling can be used to train the machine learning system 113 of the systems 100 to identify potential malignancies. In some implementations, the classification system 210 allows a user to verify whether or not the machine learning system 113 of the systems 100 correctly identified a potential malignancy. Based on the user verification, the algorithms used by the machine learning system 113 to detect potential malignancies can be updated such that accuracy of detection is increased. By providing a means to access image data corresponding to medical procedures from several sources, the cloud-computing environment 202 and the classification system 210 allows for the access to a plethora of materials that can train the machine learning system 113 of the systems 100. This vast access to training materials can facilitate the achievement of the aforementioned prediction rates (e.g., the sensitivity rate, specificity rate, etc.).

Although the shown implementation describes the system 200 as including one or more of the data processing systems 100 described in this specification, other implementations may additionally, or alternatively, includes other systems capable of transmitting images. For example, the system 200 may include one or more endoscopic towers 150, other types of computing devices, and so forth. Thus, the system 200 can be used to train the data processing systems 100 before they are deployed for use, by using images collected from other sources.

Figure 4:
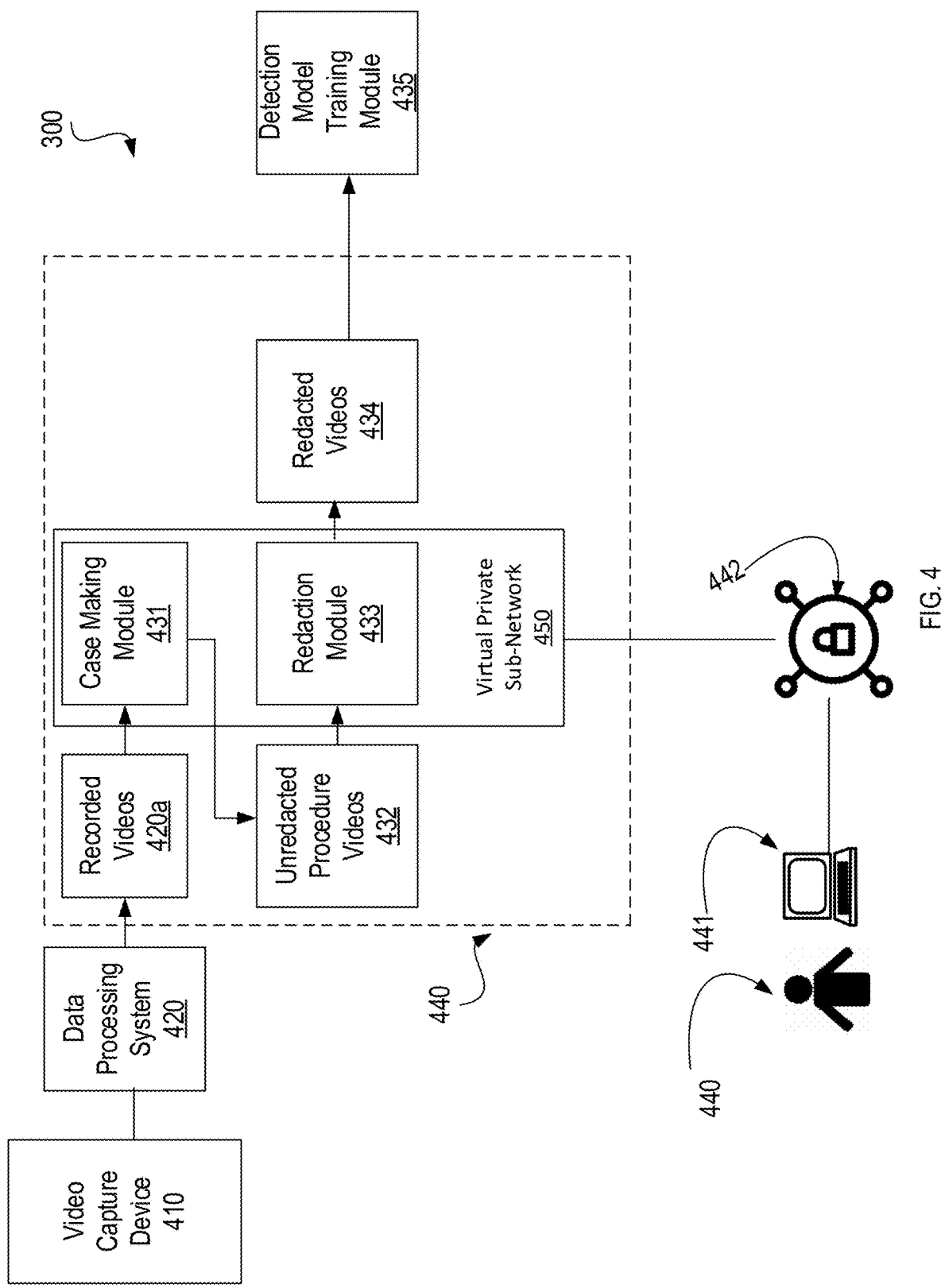
FIG. 4 shows a data processing architecture for generating cases for malignancy detection training.

FIG. 4 shows a data processing architecture 300 for generating cases for malignancy detection training. As shown in FIG. 4, a video capture device 410 is communicatively coupled with a data processing system 420. The video capture device 420 can be the video capture device 140 discussed previously with reference to FIG. 1. The data processing system 420 can be the data processing system 100 as discussed previously with reference to FIG. 1. As indicated previously with reference to FIG. 1, the video capture device 420 is configured to receive image data representing one or more images from an imaging device (i.e., endoscope) of an endoscopic tower, consolidate the one or more images, and generate video data representing the consolidated one or more images as recorded videos 420a.

The data processing system 420 is capable of receiving the video data representing the recorded videos 420a from the video capture device 410 and transmit the video data to a cloud computing environment 440. The cloud computing environment 440 can be, for example, specifically designated to a particular health care provider, such as a hospital or a clinic. The data representing the recorded videos 420a can be transmitted to a virtual private sub-network 450 of the cloud computing environment 440. The virtual private sub-network 450 can include a case making module 431 and a redaction module 433. The case making module 431 is capable of processing the data representing the recorded videos 420a to generate data representing unredacted procedure videos 432. An unredacted procedure video 432 refers to video segments that include one healthcare procedure. Thus, the case making module 431 can process the data representing the recorded videos 420a to generate segmented video data representing segmented video clips in which each video clip represents one complete medical procedure (e.g., an endoscopic procedure).

The redaction module 433 can receive the data representing the unredacted procedure videos 432, and for each individual procedure associated with the unredacted procedure videos 432, the redaction module 433 is capable of removing, from the data, information that may identify the patient corresponding to the individual procedure. For example, the redaction module 433 can identify, from the video data associated with an individual procedure, pixels that correspond to human-readable characters that may identify the patient (for example, a string of characters that identify the name of the patient, social security number of the patient, and so forth), and either remove or obfuscate those pixels (for example, by adding a blur property to those identified pixels).

The data representing the redacted videos 434 can be transmitted to a detection model training module 435, which can be used to train a machine learning system for detecting potential malignancies (such as the machine learning system 113 discussed earlier with reference to FIG. 1), as previously discussed with reference to FIG. 3 (e.g., classification system 210). A user 440 (such as, an employee of a health care provider) can use a computing device 441 to access the virtual private sub-network 450 through a virtual private network 442. When accessing the virtual private sub-network 450, the user 440 can use the case making module 431 to validate each unredacted procedure video 432 before they are transmitted to the redaction module 433 by, for example, by matching each procedure video 432 to a particular procedure using electronic health records. The user 440 can use the redaction module 433 to access the redacted videos 434 to validate that patient identification has been removed from the unredacted procedure videos 432. Once the user 440 validates that the patient identification is removed, the user 440 can use their computing device 441 to request that the data representing the redacted videos 434 be transmitted to the detection model training module 435.

Figure 5:
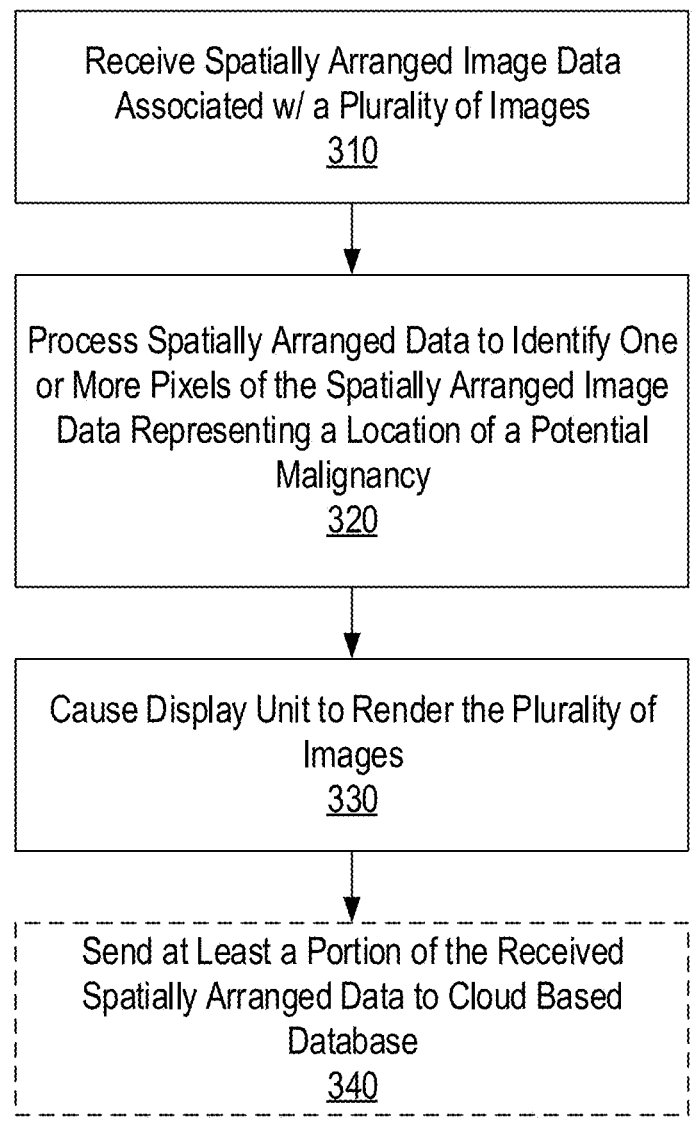
FIG. 5 shows a flow chart depicting a method for improving potential malignancy detection in individuals, according to one or more implementations of the present disclosure.

FIG. 5 shows a flow chart depicting a method 200 for improving potential malignancy detection in individuals, according to one or more embodiments of the present disclosure. For illustrative purposes, the method 200 is described as being performed by the system 100 for improving potential malignancy detection discussed previously with reference to FIG. 1. The method 200 includes receiving spatially arranged image data associated with a plurality of images (block 310), processing the spatially arranged data to identify one or more pixels of the spatially arranged image data representing a location of a potential malignancy (block 320), and causing a display unit to render the plurality of images (block 330). In some implementations, the method 200 includes sending at least a portion of the received spatially arranged data to a cloud based database (block 340).

At block 310, the computer processors 110 receive, in real-time, spatially arranged image data associated with a plurality of images from the imaging device 130. During a medical procedure, the imaging device 130 can be inserted within a patient and capture several images. The imaging device 130 can transmit spatially arranged image data corresponding with the captured images to the computer processors 110 and/or the machine learning system 113.

At block 320, the computer processors 110 generate a plurality of processed images by processing the spatially arranged image data through one or more data structures storing one or more portions of executable logic included in an artificial neural network (e.g., the machine learning system 113) to identify one or more pixels of the spatially arranged image data representing a location of a potential malignancy in an individual as the spatially arranged image data is received from the imaging device 113. In some implementations, as the image data is received, the machine learning system identifies locations of potential malignancies (e.g., polyps) using one or more of the aforementioned techniques.

At block 330, the computer processors 110 cause, in real-time, the display unit 120 to render the plurality of processed images corresponding to the image data. In some implementations, one or more of the displayed processed images includes one or more graphical overlays (e.g., overlay 122) generated by the computer processors 110 that isolates the identified locations of potential malignancies. In some implementations, if a processed image includes both a potential malignancy and a surgical tool detected by the machine learning system 113, that image does not include the one or more graphical overlays. For example, as the endoscopic tower 150 is streaming images to the computer processors 110, the computer processors 110 can be identifying locations of potential polyps and displaying the stream with overlays that isolate locations of the potential polyps. If a medical practitioner decides to insert a surgical tool (such as a cutting device/scalpel), the machine learning system 113 can detect the presence of the cutting device in the image stream and the computer processors 110 can remove the graphical overlay as to not hinder view of the surgical tool. In some implementations, the computer processors can determine an image quality metric (e.g., blurriness) of an image, and if that image quality metric fails to satisfy a metric threshold, that image does not includes the one or more graphical overlays. For example, if an image is determined to be too blurry, an overlay may not be displayed on that image.

At block 340, in some implementations, the computer processors 110 transmits the spatially arranged image data corresponding to the images captured by the imaging device 130 to a cloud-based database (or other hardware storage device), such as one of the cloud data centers 204a, 204b of the cloud-computing environment 202 discussed previously with reference to FIG. 3. The image data can be retrieved by other computing systems, such as the computing systems 220, and the corresponding images can be displayed on a user interface of the computing systems. The image data can also be retrieved by the classification system 210 to allow a user to label potential malignancies in the corresponding images and/or validate the locations of potential malignancies as identified by the machine learning system 113.

In the foregoing description, embodiments of the invention have been described with reference to numerous specific details that may vary from implementation to implementation. The description and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction. Any definitions expressly set forth herein for terms contained in such claims shall govern the meaning of such terms as used in the claims. In addition, when we use the term "further comprising," in the foregoing description or following claims, what follows this phrase can be an additional step or entity, or a sub-step/sub-entity of a previously-recited step or entity.

What is claimed is:

1. A data processing system comprising:
   a display unit;
   a memory; and
   at least one processor configured to execute one or more instructions stored in the memory to perform operations comprising:
   receiving spatially arranged image data associated with a plurality of images from an imaging device;
   generating a plurality of processed images by processing the spatially arranged image data to identify one or more pixels of the spatially arranged image data representing, a set of processed images of the plurality of processed images, a location of a potential malignancy in an individual;
   causing the display unit to display the set of processed images, wherein the set of processed images include at least one graphical overlay generated by the at least one processor;
   detecting that a surgical tool is present in at least one of the processed images while the surgical tool is present in a surgical space associated with the potential malignancy; and
   in response to the detecting,
   altering the at least one graphical overlay from the at least one of the processed images, wherein the altering of at least one graphical overlay enables the at least one graphical overlay to be removed while the surgical tool is being detected, and
   displaying an indicator when the at least one graphical overlay is displayed for less than a threshold amount of time.

2. The data processing system of claim 1, wherein an amount of time between receiving the spatially arranged image data and causing the display unit to display the set of processed images is less than 60 milliseconds.

3. The data processing system of claim 1, wherein the spatially arranged image data is received through a video capture card that is communicatively coupled to an endoscopic processing unit that comprises the imaging device.

4. The data processing system of claim 1, wherein the set of processed images that are displayed include at least one visual indicator that indicates the set of processed images correspond to spatially arranged image data that has been processed by the at least one processor.

5. The data processing system of claim 1, wherein the operations further comprise causing the display unit to display an indicator that indicates a potential malignancy has been identified in a previously displayed processed image that did not include a graphical overlay isolating one or more image locations corresponding to that potential malignancy.

6. The data processing system of claim 1, wherein the at least one graphical overlay comprises a bounding box.

7. The data processing system of claim 1, wherein the potential malignancy includes a polyp.

8. The data processing system of claim 1, wherein the imaging device includes an endoscopic imaging device.

9. The data processing system of claim 1, wherein the at least one processor is further configured to be communicatively coupled to a cloud-computing environment and to transmit the spatially arranged image data to the cloud-computing environment.

10. The data processing system of claim 1, wherein the at least one graphical overlay represents the location of the potential malignancy in the individual, wherein the indicator is configured for being displayed in at least one of the set of processed images after the at least one graphical overlay representing the location of the potential malignancy in the individual are no longer being displayed.

11. The data processing system of claim 1, the operations further comprising:
   detecting, from the spatially arranged image data associated with a plurality of images from an imaging device, patient identifying information; and
   obscuring, from the spatially arranged image data associated with a plurality of images from an imaging device, the patient identifying information.

12. The data processing system of claim 1, the operations further comprising:
   padding an input volume that includes the one or more pixels of the spatially arranged image data representing a location of a potential malignancy in an individual; and
   controlling, based on padding the input volume, a spatial size of an object included in a graphical overlay of the one or graphic overlays, the object being associated with the location of a potential malignancy in an individual.

13. The data processing system of claim 1, the operations further comprising:
causing the at least one graphical overlay to be displayed for at least a threshold amount of time for smoothing display of the graphical overlay.

14. A method comprising:
receiving spatially arranged image data associated with a plurality of images from an imaging device;
generating a plurality of processed images by processing the spatially arranged image data to identify one or more pixels of the spatially arranged image data representing, a set of processed images of the plurality of processed images, a location of a potential malignancy in an individual;
causing a display unit to display the set of processed images, wherein the set of processed images include at least one graphical overlay;
detecting that a surgical tool is present in at least one of the processed images while the surgical tool is present in a surgical space associated with the potential malignancy; and
in response to the detecting,
altering the at least one graphical overlay from the at least one of the processed images, wherein the altering of at least one graphical overlay enables the at least one graphical overlay to be removed while the surgical tool is being detected, and
displaying an indicator when the at least one graphical overlay is displayed for less than a threshold amount of time.

15. The method of claim 14, wherein the set of processed images that are displayed include at least one visual indicator that indicates the set of processed images correspond to spatially arranged image data that has been processed by at least one processor.

16. The method of claim 14, further comprising:
causing the display unit to display an indicator that indicates a potential malignancy has been identified in a previously displayed processed image that did not include a graphical overlay isolating one or more image locations corresponding to that potential malignancy.

17. The method of claim 14, wherein the at least one graphical overlay represents the location of the potential malignancy in the individual, wherein the indicator is configured for being displayed in at least one of the set of processed images after the at least one graphical overlay representing the location of the potential malignancy in the individual are no longer being displayed.

18. The method of claim 14, further comprising:
detecting, from the spatially arranged image data associated with a plurality of images from an imaging device, patient identifying information; and
obscuring, from the spatially arranged image data associated with a plurality of images from an imaging device, the patient identifying information.

19. The method of claim 14, further comprising:
padding an input volume that includes the one or more pixels of the spatially arranged image data representing a location of a potential malignancy in an individual; and
controlling, based on padding the input volume, a spatial size of an object included in a graphical overlay of the one or graphic overlays, the object being associated with the location of a potential malignancy in an individual.

20. The method of claim 14, further comprising:
causing the at least one graphical overlay to be displayed for at least a threshold amount of time for smoothing display of the graphical overlay.

\* \* \* \* \*